(12) United States Patent
Christian et al.

(10) Patent No.: US 8,545,510 B2
(45) Date of Patent: Oct. 1, 2013

(54) CLAMPING SLEEVE FOR CLAMPING A CANNULATED DRILL AND A GUIDE WIRE

(75) Inventors: Georg Christian, München (DE); Jörg Uhde, München (DE)

(73) Assignee: Brainlab AG, Feldkirchen (DE)

( * ) Notice: Subject to any disclaimer, the term of this patent is extended or adjusted under 35 U.S.C. 154(b) by 804 days.

(21) Appl. No.: 12/512,748

(22) Filed: Jul. 30, 2009

(65) Prior Publication Data
US 2010/0030221 A1 Feb. 4, 2010

Related U.S. Application Data

(60) Provisional application No. 61/104,861, filed on Oct. 13, 2008.

(30) Foreign Application Priority Data

Aug. 4, 2008 (EP) ...................... 08161738

(51) Int. Cl.
*A61B 17/58* (2006.01)
*A61B 17/60* (2006.01)
*A61F 2/00* (2006.01)

(52) U.S. Cl.
USPC .......................................................... 606/96

(58) Field of Classification Search
USPC ............. 606/96, 98, 304, 314, 309, 324, 323; 24/133, 545; 279/2.02, 19.6, 50, 95, 137, 279/46.1–46.3, 43.1–43.2; 408/241 G, 197, 408/202, 240
See application file for complete search history.

(56) References Cited

U.S. PATENT DOCUMENTS

| | | | | |
|---|---|---|---|---|
| 4,091,880 A | * | 5/1978 | Troutner et al. | 606/104 |
| 5,374,270 A | * | 12/1994 | McGuire et al. | 606/80 |
| 5,431,659 A | * | 7/1995 | Ross et al. | 606/103 |
| 5,697,935 A | * | 12/1997 | Moran et al. | 606/104 |
| 7,207,995 B1 | | 4/2007 | Vandewalle | |
| 2004/0122460 A1 | | 6/2004 | Shores et al. | |
| 2005/0074304 A1 | * | 4/2005 | Couture et al. | 408/110 |
| 2006/0286504 A1 | | 12/2006 | Maitre et al. | |

* cited by examiner

*Primary Examiner* — Andrew Yang
*Assistant Examiner* — Diana S Jones
(74) *Attorney, Agent, or Firm* — Renner, Otto, Boisselle & Sklar, LLP

(57) ABSTRACT

The present invention relates to a clamping sleeve for clamping a cannulated drill and a guide wire for medical purposes, wherein the clamping sleeve can be introduced into the chuck of a drilling machine, comprising:

at least one drill contact area which protrudes into the interior of the clamping sleeve in order to clamp the cannulated drill, through which the guide wire runs, when a force acts inwards on the outer side of the clamping sleeve;

at least one wire contact area in order to clamp an exposed part of the guide wire which is not enveloped by the cannulated drill when the force acts inwards on the outer side of the clamping sleeve;

wherein the at least one wire contact area and the at least one drill contact area lie sequentially in the longitudinal direction of the clamping sleeve.

20 Claims, 3 Drawing Sheets

CLAMPING SLEEVE FOR CLAMPING A CANNULATED DRILL AND A GUIDE WIRE

RELATED APPLICATION DATA

This application claims the priority of U.S. Provisional Application No. 61/104,861, filed on Oct. 13, 2008, which is hereby incorporated in its entirety by reference.

FIELD OF THE INVENTION

The present invention relates to a clamping sleeve for clamping a cannulated drill and a guide wire, in particular a Kirschner wire. The clamping sleeve thus in particular serves medical purposes. The clamping sleeve is intended to simultaneously clamp the cannulated drill and the guide wire, such that the cannulated drill is fixed relative to the guide wire.

BACKGROUND OF THE INVENTION

In known cannulated drills, the guide wire is guided loosely through the drill. In the known method, the guide wire serves in particular to guide the drill.

FIG. 1 schematically shows a fracture 22 or fissure 22 in a bone 20. The bone fracture 22 is fixed using two Kirschner wires 30 and 32. In the prior art, another Kirschner wire 10 is then inserted. The position of the inserted Kirschner wire 10 is checked by means of an x-ray apparatus or C-arm. If the check reveals that the position is not correct, the Kirschner wire 10 is removed and re-inserted until the check using the x-ray apparatus reveals an acceptable position of the Kirschner wire 10. An incorrect position of the Kirschner wire 10 can also result when the Kirschner wire 10 is navigated, since the Kirschner wire 10 can be bent in the bone 20. "Navigation" here means for example attaching marker elements or a marker array consisting of a number of marker elements to a part of the Kirschner wire or to an object which is fixedly connected to the Kirschner wire. In the case of a wire which is clamped in a chuck, for example, this would be the corresponding drilling machine and a marker array at the target region, for example the fractured bone. The position of the marker elements is detected by a detection device. The marker elements can actively emit beams or waves (for example, infrared beams) or passively reflect beams or waves (for example, infrared beams). The emitted or reflected beams or waves are detected by a detector (for example, an infrared camera). The position of the marker elements can thus be determined from the detection signals. Since the relative position between the marker elements and the part to be navigated (in this case, the tip of the Kirschner wire) is known, the position of the Kirschner wire 10 can be determined, but only providing the Kirschner wire 10 is not bent.

Once the position of the Kirschner wire 10 has been approved, a cannulated drill 11 is guided over the Kirschner wire, in order to create a drill hole 40—indicated in FIG. 1 by a broken line—on the bone, by means of a drilling machine. Once the drill hole has been completed, the drill is removed and a screw is threaded over the Kirschner wire in order to fix the bone fracture at the envisaged position by means of the screw. The Kirschner wire assists in correctly positioning the screw as the screw is screwed into the drilling channel produced.

SUMMARY OF THE INVENTION

It is an object of the invention to enable the guide wire to be drilled into an object together with the drill during the drilling process.

The above object is solved by a clamping sleeve for clamping a cannulated drill and a guide wire for medical purposes, wherein the clamping sleeve can be introduced into the chuck of a drilling machine, comprising: at least one drill contact area which protrudes into the interior of the clamping sleeve in order to clamp the cannulated drill, through which the guide wire runs, when a force acts inwards on the outer side of the clamping sleeve; at least one wire contact area in order to clamp an exposed part of the guide wire which is not enveloped by the cannulated drill when the force acts inwards on the outer side of the clamping sleeve; wherein the at least one wire contact area and the at least one drill contact area lie sequentially in the longitudinal direction of the clamping sleeve, and by a system consisting of the cannulated drill, the guide wire and said clamping sleeve, wherein if the clamping sleeve surrounds the cannulated drill comprising an interior guide wire, both are fixed if a force acts inwards, wherein if there is no force acting inwards, the distance between the wire contact area and the guide wire is different to, i.e. greater or smaller than, the distance between the drill contact area and the cannulated drill, and/or the clear width in the region of the drill contact areas is greater than the diameter of the drill if there is no force acting inwards, and/or the clear width in the region of the wire contact area is greater than the diameter of the guide wire if there is no force acting inwards. The dependent claims are directed to advantageous embodiments.

The clamping sleeve in accordance with the invention can advantageously be introduced into the chuck of a drilling machine. It thus lies between the inner surface of the chuck and the outer surface of the cannulated drill and the outer surface of the guide wire which is not enveloped by the cannulated drill.

The clamping sleeve preferably comprises at least one drill contact area which serves to fix the cannulated drill when the drill contact area is pressed against the cannulated drill. The drill contact area preferably protrudes into the interior of the clamping sleeve, in particular in the radial direction. The drill contact area relays a force, which acts on the outer side of the clamping sleeve and is in particular exerted by the chuck, onto the cannulated drill, such that in particular a force-fit connection between the cannulated drill and the clamping sleeve results. Alternatively or additionally, recesses or protrusions can be formed in the cannulated drill or in the drill contact area, which interlock in such a way that a positive-fit connection results.

The cannulated drill has a drilling tip which is situated at one end (the first end) of the drill. The guide wire protrudes at least from the other end (the second end). The second end of the drill comprises the drill shaft. A tip of the guide wire can in particular protrude from the first end. The drill contact area of the clamping sleeve preferably contacts the drill shaft, while the wire contact area contacts the guide wire which protrudes from the second end of the drill. A part of the drill, in particular the drilling tip, preferably protrudes from one end (the first end) of the clamping sleeve, while the guide wire in particular protrudes from the other end (the second end). The longitudinal direction of the clamping sleeve runs from the first end to the second end of the clamping sleeve. The drill contact area and the wire contact area preferably lie sequentially along this longitudinal direction. The first end is then also referred to as the first longitudinal end. The second end is then also referred to as the second longitudinal end.

The wire contact area and/or drill contact area preferably protrude inwards in the radial direction. The at least one wire contact area preferably protrudes further inwards than the at least one drill contact area. The wire contact area thus has a smaller distance from the (virtual) longitudinal axis of the clamping sleeve which runs in the longitudinal direction.

The drill contact area and wire contact area are preferably formed such that they enable and ensure a full contact, in particular a positive-fit and/or force-fit contact, with the drill and/or guide wire, in particular when an external force acting inwards is exerted on the clamping sleeve. If the drill shaft is cylindrically formed, then the surface of the drill contact area is preferably likewise cylindrical, i.e. formed as a cylindrical area portion. If the guide wire is cylindrically formed, then the surface of the wire contact area is preferably likewise cylindrically formed, i.e. in the shape of a cylindrical area portion which surrounds the guide wire. A positive-fit connection between the drill and the drill contact area and/or between the guide wire and the wire contact area can also be formed. To this end, protrusions or recesses can for example be formed along the circumference of the drill and/or guide wire, with which matching, in particular complementarily formed extensions or recesses on the clamping sleeve can engage.

Preferably, the clamping sleeve is elastically spread, i.e. it dilates in particular in the direction of the first end, wherein this dilation can be reduced or completely eliminated due to the clamping sleeve being elastically formed, in particular when an external force acts. The dilation is in particular shown by the fact that the wire contact area and/or drill contact area is inclined with respect to the longitudinal axis of the clamping sleeve. The inclination is preferably such that surface points on the surface of the wire contact area and/or drill contact area are increasingly distant from the longitudinal axis of the clamping sleeve, in the longitudinal direction of the clamping sleeve in the direction of the first end of the clamping sleeve (which is nearer to the drill tip than the second end of the clamping sleeve). The aforesaid spreading and/or inclination and the associated increasing distance from the longitudinal axis preferably obtains in the state of the clamping sleeve in which there is no force acting on it. The clamping sleeve is preferably formed such that due to the elasticity and/or deformability of the clamping sleeve, the spread state can be corrected by applying an external force, such that the surfaces of the drill contact area and/or wire contact area run parallel to the surfaces of the drill and/or guide wire. In particular, this is intended to result in a parallel profile when the drill contact area and/or wire contact area are completely in contact with the drill and/or wire, respectively.

The clamping sleeve is preferably sub-divided into sectors in its longitudinal direction. These sectors are in particular (on average) increasingly distant from the longitudinal axis of the clamping sleeve, from the second end of the clamping sleeve to the first end. At least one sector preferably comprises at least one drill contact area and at least one wire contact area. Preferably, each sector comprises at least one drill contact area and at least one wire contact area. The sectors are preferably connected to each other at one end, preferably the second end, of the clamping sleeve (for example, in a material fit and/or integrally). The sectors are spaced apart from each other over a broad region of the longitudinal extension of the clamping sleeve, in particular separated by a gap, if there is no force acting inwards on the clamping sleeve from without. This longitudinal region of the clamping sleeve for which spacing is provided between the sectors preferably extends over more than 50% of the length of the clamping sleeve, preferably over more than 80% of the length of the clamping sleeve. A spacing is preferably provided at the first end of the clamping sleeve, from where it extends in the direction of the second end. The spacing can in particular be formed as a gap which tapers from the first end to the second end.

The spacing of the sectors is preferably formed such that when a force is applied inwards from without, the sectors are moved towards each other until they mutually approach or contact each other. The drill contact area and/or the wire contact area is preferably formed such that when the sectors contact, a parallel surface of the wire contact area and/or drill contact area arises, which is parallel to the longitudinal axis of the clamping sleeve, as viewed in the longitudinal direction of the clamping sleeve.

The wire contact area is part of a wire contact portion of the clamping sleeve, which extends (radially) outwards from the wire contact area to the outer area of the clamping sleeve. The drill contact area is part of a drill contact portion of the clamping sleeve, which extends (radially) outwards from the drill contact area to the outer area of the clamping sleeve. The wire contact portion is connected to one end of the clamping sleeve, in particular the second end, by a first connecting portion. The wire contact portion is preferably also connected to the drill contact portion by a second connecting portion. The first connecting portion is preferably formed to be more elastic than the wire contact portion and/or the drill contact portion. The second connecting portion is preferably formed to be more elastic than the wire contact portion and/or the drill contact portion. In particular, the first connecting portion can exhibit a different elasticity to the second connecting portion. The first connecting portion can for example be formed to be more elastic than the second connecting portion.

The different elasticity can be realized in various ways. It can for example be realized by different wall thicknesses of the portions or by different materials. The sectors can also be formed with different widths, which can be achieved by expanding the spacing (the gaps in the region of the portions). In other words, the portions are constricted or waisted at the points where they are to be more elastic.

In one embodiment, the clamping sleeve can be configured such that, if it is for example inserted in a chuck and a force acting inwards is to be exerted on it via the chuck, the chuck only contacts a part or a region of the clamping sleeve. In particular, the embodiment can be configured such that the chuck only contacts a region of the clamping sleeve which is nearer to one of the two longitudinal ends (the first or second end) of the clamping sleeve than to the other longitudinal end. The region is in particular in the vicinity of the first (i.e. in particular flared) end of the clamping sleeve. The drill contact portion is in particular formed to be protruding with respect to at least one of the following portions: the first connecting portion; the second connecting portion; and the wire contact portion. In this way, the drill contact portion is pressed in the direction of the longitudinal axis by an application of force, while other portions are in particular not in contact with the chuck. In particular, the drill contact portion performs a sort of pivoting movement about an elastic region of the first and/or second connecting portion. Depending on how the elasticity of the first and/or second connecting portion is formed, the circumference of the pivoting movement about the first connecting portion can turn out different to that about the second connecting portion. This can be used to achieve a contact between the drill contact area and the drill and between the wire contact area and the guide wire in a desired sequence, while the chuck pushes ever further inwards, i.e. draws nearer and nearer to the longitudinal axis of the clamping sleeve.

As stated above, the clamping sleeve in accordance with the invention is preferably used in a navigated system. In this case, it is advantageous if the position of the drilling tip is known relative to the drilling apparatus (drilling machine). This is for example achieved by a calibrating step by means of a second known navigated object which can indicate the position of the drill tip relative to the marker devices fastened to the Kirschner wire.

In order to facilitate use and to validate the length calibration in a navigated application, the sleeve can additionally also comprise a stopper for the chuck, in order to prevent the sleeve from slipping into a chuck which is too large. This stopper protrudes (radially) outwards. As viewed in the longitudinal direction of the clamping sleeve, this chuck stopper is therefore nearer to the drilling tip than the chuck is.

In order to further validate the length calibration for navigation, by positioning the drill and in particular the drilling tip in a defined way relative to the clamping sleeve, an abutting area for the end of the drill is preferably provided which is also referred to here as the "drill end abutting area". This drill end abutting area is preferably part of the clamping sleeve, in particular an integral part, and preferably protrudes into the interior of the clamping sleeve in the direction of the longitudinal axis, in particular radially inwards. It in particular protrudes oblique, transverse or perpendicular to the direction of longitudinal extension of the clamping sleeve. The drill end abutting area can be part of the wire contact portion and can in particular be formed by the part of the wire contact portion which is nearest to the first end of the clamping sleeve. It can in particular be an area of the wire contact portion which faces the first end of the clamping sleeve.

The present invention is also directed to a system which, in addition to the clamping sleeve, also preferably comprises the cannulated drill and/or the guide wire. The properties already described above apply to this system, in particular when a force is applied or if there is no force applied. This system is in particular configured such that the distance between the guide wire and the wire contact area and the distance between the drill and the drill contact area are selected such that, as the force applied outwards from within increases, a force-fit contact ultimately arises between the clamping sleeve and both the drill and the guide wire. This can in particular be realized in such a way that the distances between the wire contact area and the guide wire are selected to be different to those between the drill contact area and the drill. Preferably, the distance between the drill contact area and the drill is greater than the distance between the wire contact area and the guide wire, if there is no force being exerted.

The inner diameter in the region of the drill contact area is preferably greater than the diameter of the drill, when free of any forces. The inner diameter at the wire contact area is preferably greater than the diameter of the wire, when free of any forces.

The system can also comprise a drilling machine, a drilling apparatus or a chuck, to which a marker device is in particular attached. The marker device preferably comprises a number of marker elements, in particular in a defined position relative to each other. The marker elements can actively emit signals, or can reflect signals. The signals are in particular beams or waves, for example infrared beams or ultrasound waves. The signals can be detected by a detection device, in order to determine the position of the marker device.

If an independent calibration for the position of the drill tip is not used, a known position of the drilling tip is then revealed solely by the defined position between the marker device and the drilling machine and between the drilling machine and the chuck and between the chuck and the clamping sleeve and between the clamping sleeve and the drilling tip, if the dimensions of all the objects are known, by detecting the marker device.

The invention is also directed to the use of the clamping sleeve in accordance with the invention and the system in accordance with the invention, in particular to their use for navigating a drill, in particular the drill tip, in particular relative to an object such as for example an implant or a body structure (bone, for example). The invention is preferably also directed to a navigation system which includes a data processing device and a detection device. The detection device serves to detect the aforesaid marker elements, which can for example be attached to the drilling apparatus and/or to the clamping sleeve. The detection signals are processed by the data processing device, in order to determine the position of the drill, in particular the drill tip, wherein the principles known from image-guided surgery (IGS) are in particular used.

BRIEF DESCRIPTION OF THE DRAWINGS

Other features of the invention are disclosed in the following detailed description. Features of different embodiments can be combined with each other.

DETAILED DESCRIPTION

Figure 1:
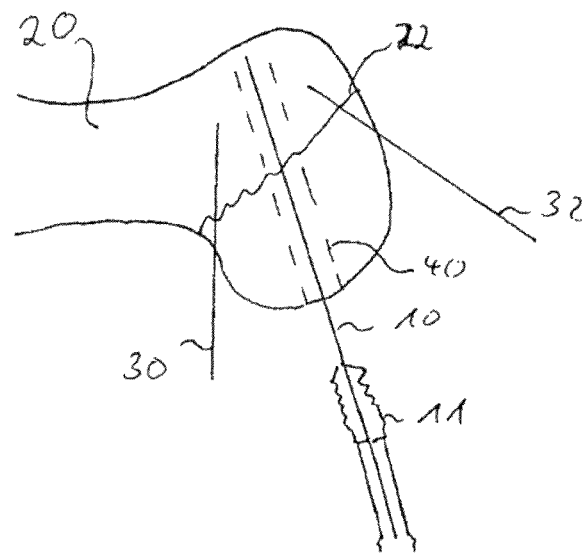
FIG. 1 shows the approach when placing a guide wire in accordance with the prior art.
Figure 2:
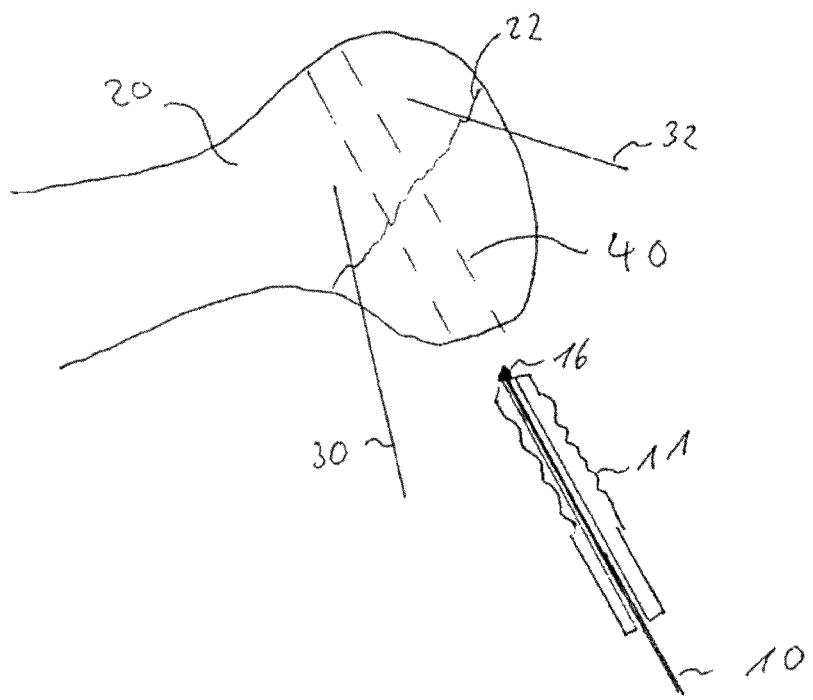
FIG. 2 shows an approach in accordance with the invention.

FIG. 2 shows an approach in accordance with the invention. The bone fracture is preferably fixed in advance using the Kirschner wires 30 and 32. Instead of a conventional drill, however, a navigated drill comprising a marker device is used, such that the position of the drilling tip relative to the bone is known at any time, i.e. as opposed to the prior art, multiple attempts using a Kirschner wire are not required. The Kirschner wire 10 is guided through the cannulated drill 11. A tip 16 of the Kirschner wire 10 can protrude from the tip of the drill 11. FIG. 2 shows the situation before the drill 11 is inserted into the bone 20 in order to create the drilling channel 40.

Proceeding from the situation shown in FIG. 2, the cannulated drill 11 is simultaneously introduced into the bone together with the Kirschner wire 10. Since the cannulated drill is navigated (for example, according to the principles of image-assisted navigation in IGS surgery (image-guided surgery)), the drill hole 40 can be created in the predetermined position, and the Kirschner wire can in particular be positioned exactly. If the drill is introduced together with the Kirschner wire, then the Kirschner wire can be knocked firmly into the bone before the cannulated drill 11 is withdrawn.

Cannulated drills are commonly available to the surgeon. If he navigated them while drilling the drill hole, he could achieve a drill hole at the desired location even without Kirschner wires. However, the cannula in the drill then becomes clogged with bone material, which impedes the drilling process. The guiding assistance of the Kirschner wire when introducing the screw is also missing.

Figure 3:
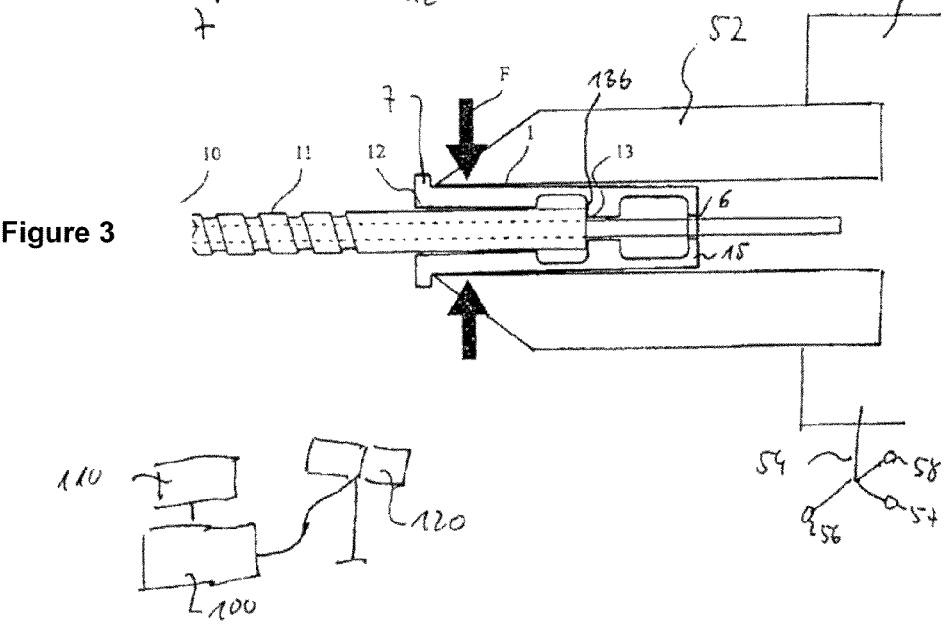
FIG. 3 shows a system in accordance with the invention, in accordance with a preferred embodiment, which comprises a clamping sleeve in accordance with the invention.

If a surgeon inserted the Kirschner wire loosely in the cannulated drill, in order to prevent the above, the Kirschner wire would be pushed away from the drilling tip by the bone material during the drilling process. In accordance with the invention, the Kirschner wire is therefore fixed relative to the cannulated drill. FIG. 3 shows how this is achieved in accordance with an embodiment in accordance with the invention.

A clamping sleeve 1 in accordance with the invention is for example pressed inwards by a force F. The clamping sleeve 1 is formed such that the force F creates at least a force-fit contact between the guide wire 10 and the clamping sleeve 1 and between the cannulated drill 11 and the clamping sleeve 1. More specifically, two contact areas are provided. A drill contact area 12 contacts the drill 11, in order to achieve a force-fit connection with the drill 11. A wire contact area 13 contacts the guide wire 10, in order to achieve a force-fit connection with the guide wire 10. The force F is applied by the chuck of a drilling apparatus or drilling machine. To this end, the arrangement shown in FIG. 3 is inserted into the chuck 52 of the drilling machine 50 or drilling apparatus 50. The guide wire 10 can in particular run through the drilling apparatus 50. A marker device 54 comprising marker elements 56, 57 and 58 can be attached to the drilling machine 50. This marker device can be detected using a detection device (not shown) of a navigation system for navigating instruments. By detecting the marker device, it is then possible to navigate the drill and in particular the drilling tip. The chuck 52 abuts a stopper 7, formed in the manner of a flange, at the first end of the clamping sleeve 1. This results in a known relative position between the clamping sleeve 1 and the marker device 54. Furthermore, the drill 11 abuts the drill end abutting area 13b which is situated to the left of the wire contact area 13 in FIG. 3. This results in a known relative position between the clamping sleeve 1 and the drill 11. Since the distance between the drilling tip at one end of the drill and the other end of the drill 11 is known, the relative position between the drill tip and the marker device 54 is therefore known, such that the drill tip can be navigated by detecting the marker device 54. In order to register the drilling tip in the reference frame of the navigation system, and in particular in order to determine the position of the drilling tip relative to the marker device, a scanning process is preferably performed in which the position of surface points or regions of the drilling tip and/or drill 11 and/or clamping sleeve 1 are detected. To this end, a calibrating matrix is for example used such as is commonly used when calibrating/validating tools or implants. This calibrating matrix can in particular be used to determine the position of the tip and the shape of the instrument—in this case, the drilling tip and/or drill and/or clamping sleeve. As an alternative to the aforementioned approach, the drill tip can for example be detected by the navigation system using a so-called pointer or any other tool having a known geometry. The pointer or tool comprises at least two markers which, when detected, allow the position of a specific point, for example the pointer tip, to be determined. If the defined point abuts the drilling tip, the position of the drill tip is therefore detected. In particular, it is registered in the reference frame of the navigation system. The position of the drilling tip relative to the marker device 54 is in particular therefore known.

As shown in FIG. 3, the marker device 54 can be detected by means of a detection device 120. The detection device 120 is part of a navigation system which in particular comprises a data processing device 100 which processes the detected signals in order to determine the location of the marker arrays or marker devices. The navigation system can in particular determine the location of the drill tip. The monitor 110 can be used to display the location of the drill tip, for example relative to a bone 20 on which a marker device can for example also be arranged.

Figure 4:
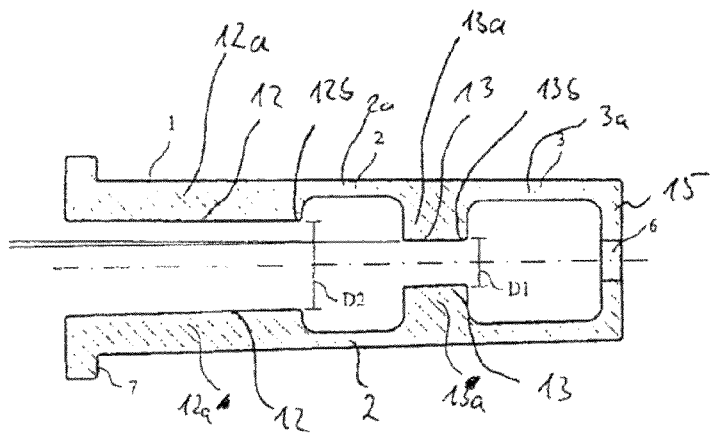
FIG. 4 shows a cross-section through the clamping sleeve in accordance with the invention.

FIG. 4 shows a clamping sleeve 1 in cross-section. The longitudinal axis of the clamping sleeve is shown by a dot-dash line. The clamping sleeve is flared to the left, at an angle α relative to the longitudinal axis. The contact areas 12 and 13 are connected via a stay 2. The wire contact area 13 is connected to the right-hand end 15 via a stay 3. The right-hand end 15 faces the drilling apparatus 50. The stays or connecting portions 2 and 3 can have different lengths and/or different thicknesses and/or can be formed from different materials. In this way, a rigidity or elasticity can arise between the end 15 and the wire contact area 13 which is different from the rigidity or elasticity provided between the wire contact area 13 and the drill contact area 12. By setting a different elasticity and/or by setting the aperture angle α and/or by the size of the clear widths D1 and D2, it is possible to set the applied external force F at which contact arises between the wire contact area 13 and the guide wire 10 and between the drill contact area 12 and the cannulated drill 11 and/or the extent to which the clamping sleeve has to be pressed together in order to ensure said contact.

The connecting portions or stays 2 and 3 are in particular formed to be more elastic than the regions 12a and 13a which respectively lie radially outwards from the contact areas 12 and 13.

Figure 6:
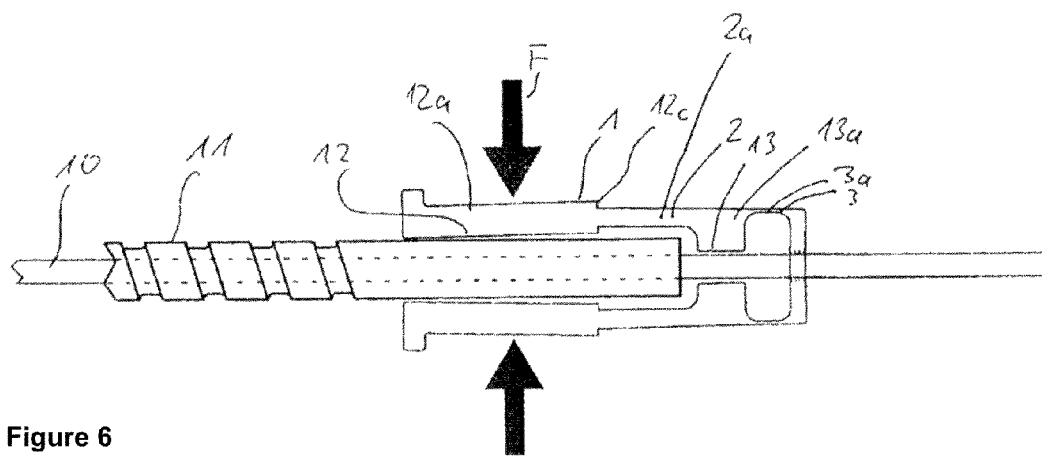
FIG. 6 shows another embodiment of the system in accordance with the invention, which comprises a clamping sleeve in accordance with the invention.

If a force F is then exerted on the clamping sleeve 1 via a chuck, as shown in FIG. 3, the end of the clamping sleeve facing the drill side (the left-hand end, see FIG. 3) pivots inwards, such that an angle β (not shown) between the drill contact area and the longitudinal axis of the clamping sleeve is reduced in the direction of longitudinal extension of the clamping sleeve. In the situation shown in FIG. 4, without the application of an external force, the angle β is equal to the angle α shown. Thus, the clamping sleeve is preferably elastically formed and allows the sleeve to pivot about the end 15 facing away from the drill (the right-hand end, see FIG. 3), such that the angle β is reduced. The angle α is the angle between the wire contact area and the longitudinal axis, as viewed in the direction of longitudinal extension of the clamping sleeve. As the force F increases, this angle α is initially reduced less than the angle β, as shown in FIG. 6. This is due to the fact that the force F also causes a pivoting movement about approximately the middle of the stay 2.

If a force is then applied to the clamping sleeve 1, this results in the pivoting movement described above, until a right-hand end 12b of the drill contact area (i.e. an end facing the drill) comes into contact with the drill and/or until a right-hand end 13b of the wire contact area comes into contact with the guide wire. Since the connecting portions 2 and 3 are formed to be more elastic than the portions 12a and 13a, which are assigned to the drill contact area or the wire contact area, respectively, a flexing or pivoting process can be performed about approximately the middle 2a and 3a of the connecting portions 2 and 3 as the force F is increased, until the drill contact area 12 fully abuts the drill 11 and the wire contact area 13 fully abuts the guide wire 10.

Figure 5:
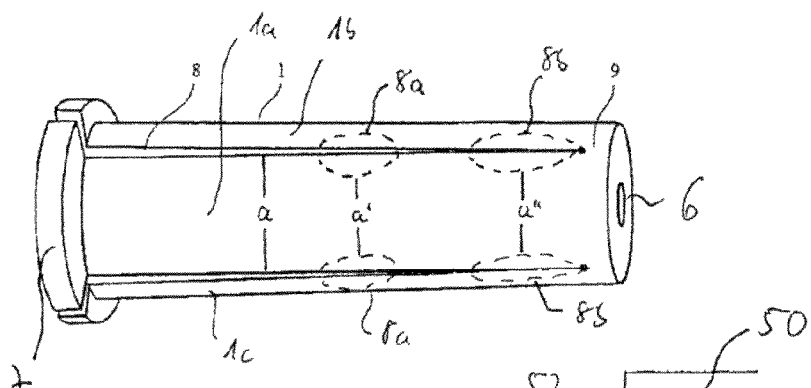
FIG. 5 shows a three-dimensional view of the clamping sleeve in accordance with the invention.

FIG. 5 shows an exterior view of the clamping sleeve in accordance with the invention. The clamping sleeve is subdivided into various sectors in its longitudinal direction. The sectors are separated by slits 8 which taper in the longitudinal direction. The slits 8 taper to the right, i.e. in the direction of the drill. The individual sectors are connected to each other at the right-hand end 9. If the sectors are pressed together by the application of an external force, for example by a chuck, such that the slits close, then the exterior shape of the clamping sleeve can preferably become cylindrical. Preferably, the wire contact areas and/or the drill contact areas in particular form closed cylindrical areas along the circumference, when pressed together.

A protrusion is situated at the left-hand end of the clamping sleeve facing away from the drill, which protrudes radially outwards and in particular serves as a stopper area 7 for the chuck 52, more specifically as a stopper area 7 for the end of the chuck 52 which faces away from the drilling apparatus. This is shown in FIG. 3. The extension which protrudes radially outwards and forms the stopper area 7 is for example formed in a similar way to a flange. An opening 6 is situated at the other end of the clamping sleeve and is provided in order to guide the guide wire 10 through, as is evident from FIG. 3. In FIG. 5, an alternative embodiment of the slits is indicated by broken lines, in accordance with which the slits 8 do not taper continuously from left to right but rather comprise cavities 8a and 8b. These cavities 8a and 8b mean that a sector 1a of the clamping sleeve in the region of the connecting portions 2 and 3 becomes narrower in the circumferential direction of the clamping sleeve. While the sector 1a has a width a in the circumferential direction outside the connecting portions 2 and 3, this width is reduced to the width a' and a" in the region of the connecting portions 2 and 3 due to the cavities 8a and 8b. This leads to an increased elasticity of the sector portion in the region of the connecting portions 2 and 3.

FIG. 6 shows another embodiment. The connecting portions 2 and 3 are formed differently in FIG. 6 than in FIG. 3. In FIG. 3, they are shown to have the same thickness. In FIG. 6, the connecting portion 2 is thicker than the connecting portion 3. This means that the connecting portion 2 is more rigid than the connecting portion 3. Therefore, when an external force F is applied, kinking occurs first and/or more strongly in a middle region 3a of the connecting portion 3. The middle region 2a of the connecting portion 2 kinks less and/or only when the force is further increased. If the distance between the drill contact area 12 and the drill 11 and between the wire contact area 13 and the guide wire 10 is suitably selected, this results in the wire contact area 13 likewise fully abutting the guide wire 10 when the drill contact area 12 fully abuts the drill contact area 12. Due to the greater elasticity of the region 3a as compared to the region 2a, and since the portion 12a assigned to the drill contact area 12 protrudes radially outwards with respect to the portion 13a assigned to the wire contact area (and in particular also with respect to the connecting portions 2 and 3), the force F acts on this portion 12a first. This leads to a pivoting or flexing process about the region 3a, which is formed to be more deformable or elastic than the portion 2a. This results in a contact between the left-side end of the portion 12a and the cannulated drill 11 first. If further force is applied, the contact area 12 becomes more and more parallel to the direction of longitudinal extension of the drill 11. This simultaneously means that the wire contact area is lowered further and further, until it finally likewise contacts the guide wire 10, such that a force-fit connection between the clamping sleeve and the guide wire results. If it is lowered further until a force fit and positive fit exists between the contact area 12 and the cannulated drill 11, this results in the maximum achievable clamping force on the force-fit and positive-fit connection between the clamping jaw 13 and the wire.

Figure 7:
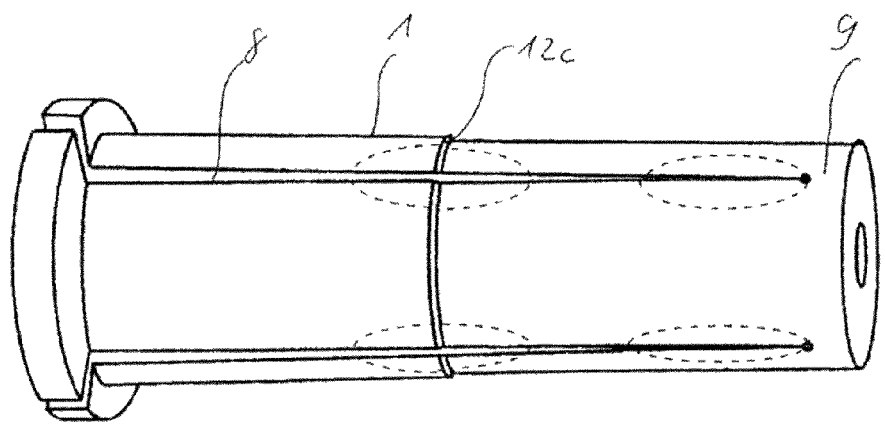
FIG. 7 shows an exterior (three-dimensional) view of the clamping sleeve of FIG. 6.

The portion 12a belonging to the drill contact area protrudes outwards by an edge 12c. This edge 12c is also clearly shown in the exterior view of the clamping sleeve 1 in FIG. 7. The clamping sleeve 1 is otherwise designed as shown in FIG. 5.

Figure 8:
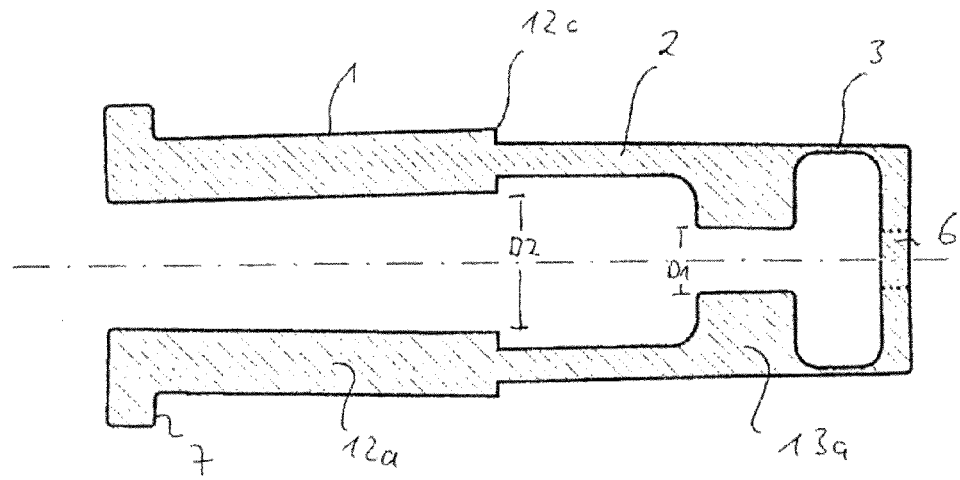
FIG. 8 shows a cross-sectional view of the clamping sleeve of FIG. 6.

FIG. 8 shows again, in an enlargement, the cross-section of the clamping sleeve such as is shown in FIG. 6. The clear widths D1 and D2, which are defined by the drill contact area 12 and the wire contact area 13, respectively, are suitably selected in order to achieve a full contact with the drill or guide wire when a force is applied.

Computer program elements of the invention may be embodied in hardware and/or software (including firmware, resident software, micro-code, etc.). The computer program elements of the invention may take the form of a computer program product which may be embodied by a computer-usable or computer-readable storage medium comprising computer-usable or computer-readable program instructions, "code" or a "computer program" embodied in said medium for use by or in connection with the instruction executing system. Within the context of this application, a computer-usable or computer-readable medium may be any medium which can contain, store, communicate, propagate or transport the program for use by or in connection with the instruction executing system, apparatus or device. The computer-usable or computer-readable medium may for example be, but is not limited to, an electronic, magnetic, optical, electro-magnetic, infrared or semiconductor system, apparatus, device or medium of propagation, such as for example the Internet. The computer-usable or computer-readable medium could even for example be paper or another suitable medium on which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiment(s).

Although the invention has been shown and described with respect to one or more particular preferred embodiments, it is clear that equivalent amendments or modifications will occur to the person skilled in the art when reading and interpreting the text and enclosed drawing(s) of this specification. In particular with regard to the various functions performed by the elements (components, assemblies, devices, compositions, etc.) described above, the terms used to describe such elements (including any reference to a "means") are intended, unless expressly indicated otherwise, to correspond to any element which performs the specified function of the element described, i.e. which is functionally equivalent to it, even if it is not structurally equivalent to the disclosed structure which performs the function in the example embodiment(s) illustrated here. Moreover, while a particular feature of the invention may have been described above with respect to only one or some of the embodiments illustrated, such a feature may also be combined with one or more other features of the other embodiments, in any way such as may be desirable or advantageous for any given application of the invention.

What is claimed is:

1. A clamping sleeve for clamping a cannulated drill bit and a guide wire for medical purposes, wherein the clamping sleeve can be introduced into a chuck of a drilling machine, the clamping sleeve comprising:

at least one radially inwardly deflectable drill contact area having a radially inner surface for engaging the cannulated drill bit, the drill contact area protruding into an interior of the clamping sleeve and configured to clamp the cannulated drill bit, through which the guide wire runs, when a force acts inwards on an outer side of the clamping sleeve; and at least one radially inwardly deflectable wire contact area having a radially inner surface for clamping an exposed part of the guide wire which is not enveloped by the cannulated drill bit when the force acts inwards on the outer side of the clamping sleeve;

wherein the interior of the clamping sleeve is open to both ends;

wherein the at least one radially inwardly deflectable drill contact area is longitudinally offset from the at least one radially inwardly deflectable wire contact area; and wherein the clamping sleeve includes a connecting portion between the radially inwardly deflectable drill contact area and the radially inward deflectable wire contact area, the connecting portion having a radially inner diameter which is larger than a radially inner diameter of the radially inwardly deflectable wire contact area and a radially inner diameter of the radially inwardly deflectable drill contact area.

2. The clamping sleeve according to claim 1, wherein the guide wire is a Kirschner wire.

3. The clamping sleeve according to claim 1, wherein the at least one radially inwardly deflectable wire contact area protrudes radially inwardly further than the at least one radially inwardly deflectable drill contact area.

4. The clamping sleeve according to claim 1, wherein the at least one radially inwardly deflectable wire contact area and the at least one radially inwardly deflectable drill contact area are formed as a cylindrical area portion having a cylindrical radius, wherein the cylindrical radius of the at least one wire contact area is smaller than the cylindrical radius of the at least one drill contact area.

5. The clamping sleeve according to claim 1, wherein at least one of the at least one radially inwardly deflectable wire contact area or the at least one radially inwardly deflectable drill contact area are formed such that their surface points are increasingly distant, continuously or incrementally at least in portions, from a longitudinal axis of the clamping sleeve in the longitudinal direction of the clamping sleeve in the direction of a first longitudinal end of the clamping sleeve, if there is no force acting inwards.

6. The clamping sleeve according to claim 1, wherein the clamping sleeve comprises sectors running in the longitudinal direction, which comprise the at least one radially inwardly deflectable drill contact area and the at least one radially inwardly deflectable wire contact area and run from the first longitudinal end of the clamping sleeve to an end portion of the clamping sleeve which lies at a second longitudinal end of the clamping sleeve, wherein the sectors are spaced apart from each other when there is no force acting inwards.

7. The clamping sleeve according to claim 6, wherein at least one of the at least one radially inwardly deflectable wire contact area or the at least one radially inwardly deflectable drill contact area are formed such that their surface points run parallel to the longitudinal axis of the clamping sleeve in the longitudinal direction of the clamping sleeve in the direction of the first longitudinal end, if the sectors approach or contact each other due to a force acting inwards.

8. The clamping sleeve according to claim 6, wherein the sectors are formed to be elastic, such that a force acting radially inwards can move the sectors into contact, at least partially by overcoming the spacing.

9. The clamping sleeve according to claim 1, wherein a wire contact portion comprises one of the at least one radially inwardly deflectable wire contact areas and is connected to a second longitudinal end of the clamping sleeve via a first connecting portion and to a drill contact portion by a second connecting portion, wherein the drill contact portion comprises one of the at least one radially inwardly deflectable drill contact areas and at least a part of at least one of the first or second connecting portion is formed to have a greater elasticity than the drill contact portion and/or the wire contact portion.

10. The clamping sleeve according to claim 1, wherein a drill contact portion of the clamping sleeve, which comprises the at least one radially inwardly deflectable drill contact area but not the at least one radially inwardly deflectable wire contact area, at least one of exhibits a different outer diameter than a wire contact portion, which comprises the wire contact area but not the drill contact area, when there is not any external force on the clamping sleeve, has the outer diameter of the drill contact portion that is greater than that of the wire contact portion, or has exterior surface points of the clamping sleeve that are increasingly distant, continuously or incrementally at least in portions, from a longitudinal axis of the clamping sleeve in the direction of a first longitudinal end of the clamping sleeve.

11. The clamping sleeve according to claim 1, wherein the wire contact portion comprises a drill end abutting area which lies between one of the at least one radially inwardly deflectable drill contact areas and one of the at least one radially inwardly deflectable wire contact areas in the longitudinal direction of the clamping sleeve and protrudes inwards, perpendicular or transverse to the longitudinal direction of the clamping sleeve, but does not protrude further inwards than the wire contact area.

12. The clamping sleeve according to claim 1, comprising a chuck stopper which protrudes radially outwards at the first longitudinal end of the clamping sleeve.

13. A system consisting of the cannulated drill bit, the guide wire and the clamping sleeve according to claim 1, wherein if the clamping sleeve surrounds the cannulated drill bit comprising an interior guide wire, both are fixed if a force acts inwards, wherein if there is no force acting inwards, at least one of the distance between the wire contact area and the guide wire is different than the distance between the radially inwardly deflectable drill contact area and the cannulated drill bit, a width in the region of the drill contact areas is greater than the diameter of the drill, or the width in the region of the radially inwardly deflectable wire contact area is greater than the diameter of the guide wire.

14. The system according to claim 13, further comprising a drilling apparatus including a chuck, wherein the clamping sleeve can be introduced into the chuck and wherein a marker device is attached to the drilling apparatus.

15. A navigated system, comprising: a data processing device and a detection device for detecting markers; and the clamping sleeve according to claim 1 or the system according to claim 13.

16. The clamping sleeve according to claim 1, further including resiliently deflectable sectors that move relative to one another between an expanded position to allow for insertion of the drill bit and guide wire and a radially collapsed position for clamping the drill and guide wire.

17. The clamping sleeve according to claim 1, wherein the connecting portion includes a reduced thickness portion between the drill contact area and the wire contact area.

18. The clamping sleeve according to claim 17, wherein the reduced thickness portion has a radially inner diameter that is greater than the radially inner diameter of the wire contact area and the radially inner diameter of the drill contact area.

19. The clamping sleeve according to claim 18, wherein a first end of the clamping sleeve is open to receive the guide wire and a second end of the clamping sleeve is open to receive the guide wire and the drill bit.

20. The clamping sleeve according to claim 19, wherein the clamping sleeve includes a reduced thickness portion between the wire contact area and the first end, the reduced thickness portion having a radially inner diameter that is greater than the radially inner diameter of the wire contact area and a radially inner diameter of the first end.

* * * * *